United States Patent [19]
Pappas et al.

[11] Patent Number: 5,702,466
[45] Date of Patent: Dec. 30, 1997

[54] ROTATIONAL AND TRANSLATIONAL BEARING COMBINATION IN BIOLOGICAL JOINT REPLACEMENT

[75] Inventors: Michael J. Pappas, Caldwell; Frederick F. Buechel, South Orange, both of N.J.

[73] Assignee: Biomedical Engineering Trust I, South Orange, N.J.

[21] Appl. No.: 648,627

[22] Filed: May 16, 1996

Related U.S. Application Data

[63] Continuation of Ser. No. 203,657, Feb. 25, 1994, which is a continuation of Ser. No. 872,954, Apr. 23, 1992, abandoned.

[51] Int. Cl.⁶ ..................................................... A61F 2/38
[52] U.S. Cl. ........................... 623/20; 623/11; 623/18
[58] Field of Search ................................... 623/11, 16, 18, 623/19, 20, 21, 39

[56] References Cited

U.S. PATENT DOCUMENTS

| | | |
|---|---|---|
| 4,007,495 | 2/1977 | Frazier . |
| 4,219,893 | 9/1980 | Noiles . |
| 4,309,778 | 1/1982 | Buechel et al. . |
| 4,340,978 | 7/1982 | Buechel et al. . |
| 4,353,136 | 10/1982 | Polyzoides et al. . |
| 4,470,158 | 9/1984 | Pappas et al. . |
| 4,728,332 | 3/1988 | Albrektsson . |
| 4,950,297 | 8/1990 | Elloy et al. . |
| 5,370,701 | 12/1994 | Finn . |
| 5,395,401 | 3/1995 | Bahler . |

FOREIGN PATENT DOCUMENTS

| | | |
|---|---|---|
| 0 186 471 | 7/1986 | European Pat. Off. . |
| 0 349 173 | 1/1990 | European Pat. Off. . |
| 0 529 408 A1 | 3/1993 | European Pat. Off. . |
| 0 519 873 | 1/1996 | European Pat. Off. . |
| 2 663 536 | 12/1991 | France . |
| 25 45 821 | 4/1976 | Germany . |
| 25 50 704 | 5/1976 | Germany . |
| 35 29 894 | 3/1987 | Germany . |
| 91 10 504.8 | 12/1991 | Germany . |
| 2 223 950 | 4/1990 | United Kingdom . |
| WO 92/08424 | 5/1992 | WIPO . |

OTHER PUBLICATIONS

EPO Search Report—Application No. EP 92810510—Sep. 21, 1993.

*Primary Examiner*—John G. Weiss
*Assistant Examiner*—P. Zuttarelli
*Attorney, Agent, or Firm*—Anthony J. Casella; Gerald E. Hespos

[57] ABSTRACT

A joint prosthesis having a femoral element, a tibial element and a bearing for articulation therebetween is disclosed to further include an intermediate element. The intermediate element permits rotation of the bearing with respect to the tibial element and longitudinal translation of the bearing with respect to the intermediate element. Transverse translation of the bearing with respect to the intermediate element is precluded. In an alternative embodiment, the longitudinal translation may be limited either in the anterior or posterior direction.

28 Claims, 6 Drawing Sheets

ROTATIONAL AND TRANSLATIONAL BEARING COMBINATION IN BIOLOGICAL JOINT REPLACEMENT

This application is a continuation of application Ser. No. 08/203,657 filed on Feb. 25, 1994 which is now pending and which is a continuation of application Ser. No. 07/872,954 filed Apr. 23, 1992 which is now abandoned.

TECHNICAL FIELD

This invention relates to prosthetic joints generally and is disclosed in the context of a prosthesis for replacement of a dysfunctional knee joint.

BACKGROUND OF THE INVENTION

Significant research has been undertaken in recent years directed to the development of joint prostheses which are reliable, i.e. prostheses which are not subject to unacceptable dislocation, not subject to bearing failure, not subject to loosening from the bones and which provide a substantial duplication of the motion of the natural joint. Typical of the joint prostheses which have been developed by others is that disclosed in U.S. Pat. No. 4,219,893 to Noiles.

Extremely successful joint endoprostheses are disclosed in our prior patents. Specifically, rotating platform bearing prostheses are disclosed in our prior U.S. Pat. No. 4,470,158. Meniscal bearing prostheses are disclosed in our prior U.S. Pat. No. 4,309,778 and our prior U.S. Pat. No. 4,340,978. As will be recognized by those skilled in these arts, the meniscal bearing prostheses are indicated for bi-cruciate retention applications, uni-condylar applications and for posterior cruciate retention applications. The rotating platform bearing prostheses are indicated where neither posterior nor anterior cruciates are retained, and in some circumstances where the posterior cruciate is viable. The present invention constitutes an improvement with respect to the inventions of our aforesaid patents and their disclosures are incorporated herein by reference. In particular, the present invention relates to a refinement of our rotating platform bearing prostheses, particularly as they may be indicated for posterior cruciate retention applications for which indications our meniscal bearing prostheses are being used.

The aforesaid patented prostheses have enjoyed widespread recognition among orthopedic surgeons and their patients. In knee replacement applications the congruency between the mating surfaces of the femoral components and their associated bearings has resulted in outstanding load distribution with attendant improved wear characteristics and operation. The geometry for achieving these congruencies is fully disclosed in the aforesaid patents and needs no further disclosure here.

Notwithstanding the unusual success of and reception achieved by our prior prostheses, we feel that certain refinements are appropriate, particularly where the posterior cruciate is viable and is to be retained. It has been found that when the anterior cruciate is absent the deficiency in the soft tissue constraint against the posterior motion of the femur on the tibia can produce undesirable increased motion and forces on a meniscal bearing, it being recognized that such meniscal bearing prostheses were designed for use where both cruciates are functioning. For example, with excess posterior motion during flexion resulting from the loss of the anterior cruciate, the meniscal bearing of our prior device can impinge upon the tibia, often stopping the posterior displacement of the bearing. Further tendency to posterior displacement may result in undesirable loading of the rim of the bearing which may result in premature bearing failure. A worst case situation might occur in instances of traumatic stress, e.g. where a patient falls and violently twists a leg. In such events the present meniscal bearing elements may be dislocated. This has been experienced in about one percent (1%) of the patients.

The alternative approach to situations where a viable posterior cruciate makes its retention desirable has been to use slightly modified rotating platform bearing prostheses. The modification has involved providing a notch in the posterior bearing and tibial components to accommodate the passage of the posterior cruciate. The result, of course, is a rotating but non-translating bearing. Therefore, during flexion, where the femur normally rolls back on the tibia due to the action of the viable posterior cruciate, the congruency between the bearing and the femoral element resists such roll-back and the flexion is inhibited. If the posterior cruciate is lax, whether because of deterioration or because such laxity has been introduced, the flexion may be uninhibited, but the desirable and natural roll-back of the femur is constrained.

Thus, roll-back and adequate congruency cannot reliably be both achieved.

SUMMARY OF THE INVENTION

It is an object of the present invention, therefore, to provide a joint prosthesis which significantly reduces the likelihood of dislocation of the bearing element, even in response to traumatic stress.

Another object of the present invention is to provide a joint prosthesis which incorporates a rotating platform bearing but which permits that bearing selectively to translate.

A specific object of the present invention as it may be incorporated in a knee prosthesis is to provide a prosthesis uniquely suitable for indications of posterior cruciate retention, where the bearing element may rotate and selectively translate and wherein the likelihood of dislocation of the bearing element is substantially eliminated.

These objects and others not enumerated are achieved by the prosthetic joint of the present invention, one embodiment of which may include a first element for attachment to a first bone, the first element having a surface facing away from the first bone; a second element for attachment to a second bone, the second element having a surface facing generally away from the second bone; a bearing element disposed between and in articulating contact with the first and second elements; and means intermediate the first element and the bearing element for selectively permitting translation and rotation of the bearing element, i.e. in two degrees of freedom while precluding lateral movement of the bearing, the intermediate means being movable with respect to both the first element and the bearing element.

BRIEF DESCRIPTION OF THE DRAWINGS

A more complete understanding of the present invention may be had from the following detailed description, particularly when read in view of the drawings wherein.

DETAILED DESCRIPTION

The preferred embodiment of the joint prosthesis according to the present invention is disclosed hereafter in the context of a total knee replacement prosthesis. It will be recognized by those skilled in these arts, however, that joint prostheses according to this invention may be utilized as prostheses for joints other than knee joints, e.g. ankles, wrists, elbows, fingers and the like.

Figure 1:
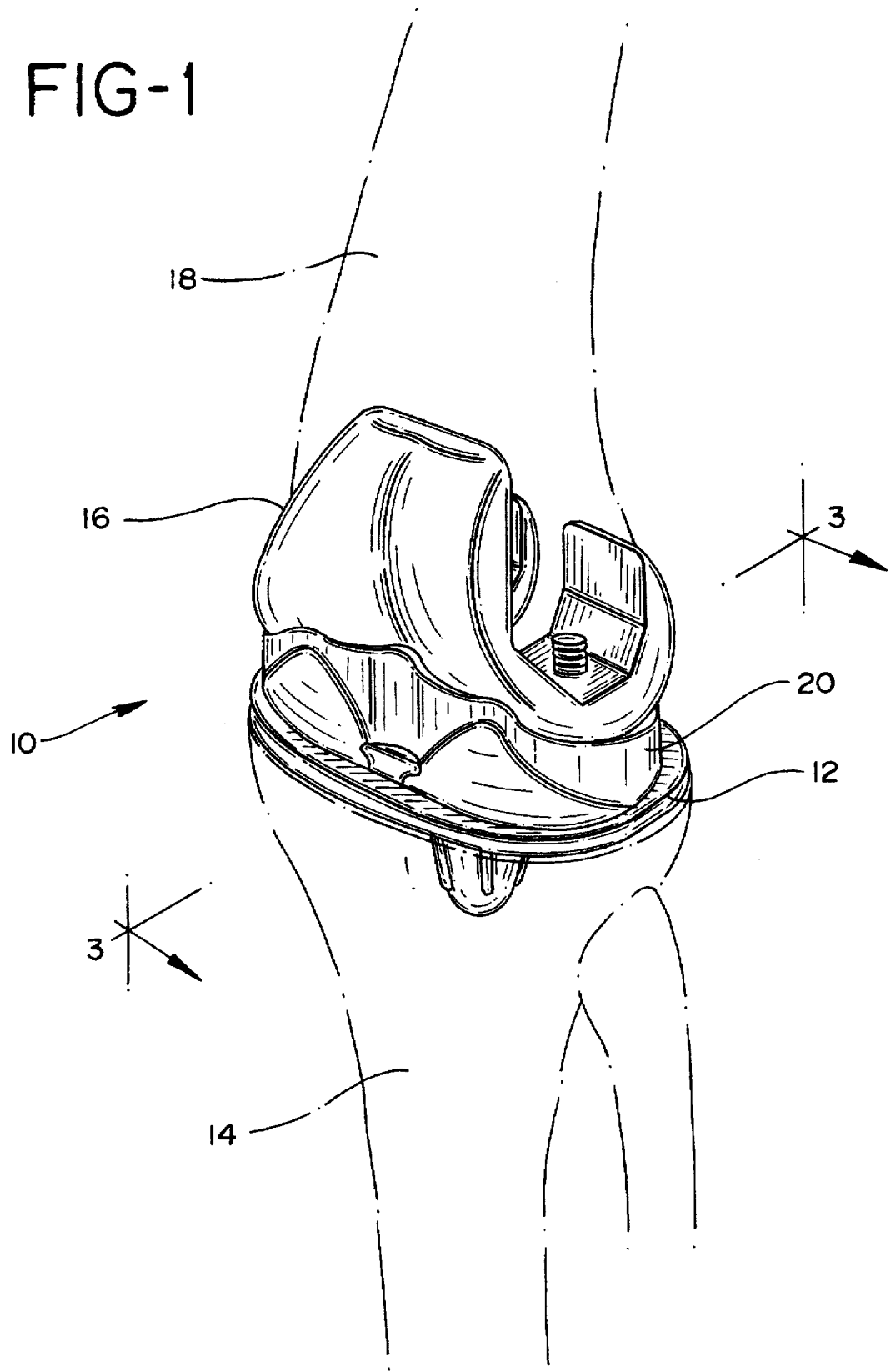
FIG. 1 is a perspective view of a prosthesis according to the present invention used as a knee prosthesis, the relevant bone structure being shown in phantom lines.
Figure 2:
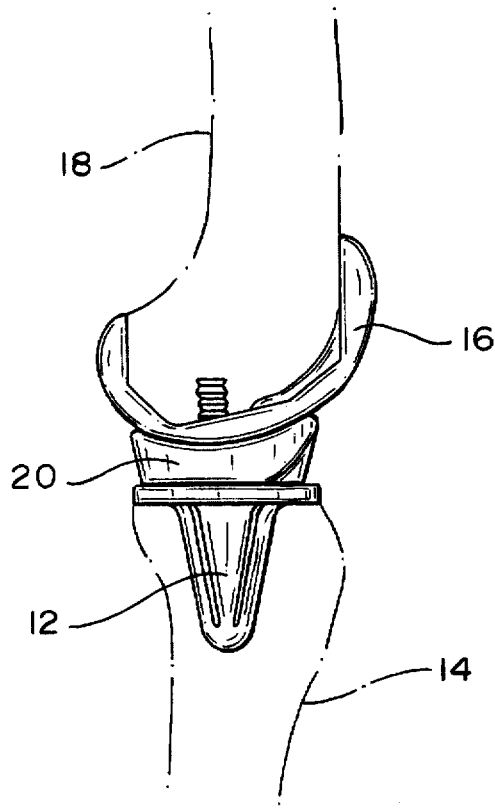
FIG. 2 is a side elevational view of the prosthesis of FIG. 1 slightly flexed.
Figure 3:
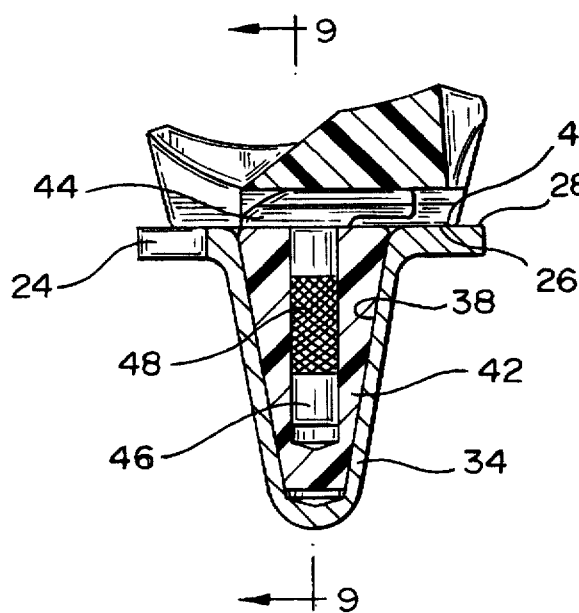
FIG. 3 is a partial elevational cross-sectional view of the prosthesis of FIG. 1, those portions shown in cross-section being depicted through the plane 3—3 of FIG. 1.
Figure 5:
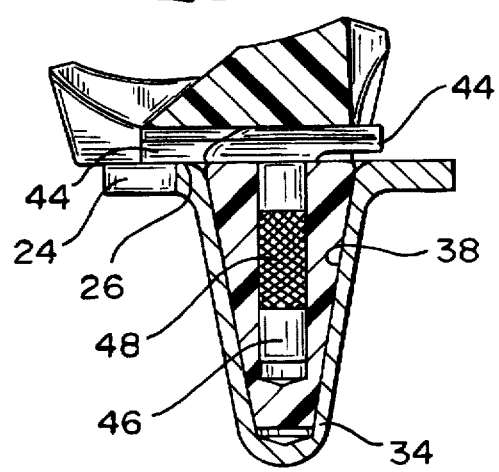
FIG. 5 is a view similar to FIG. 3 but showing the joint as flexed in FIG. 4.
Figure 6:
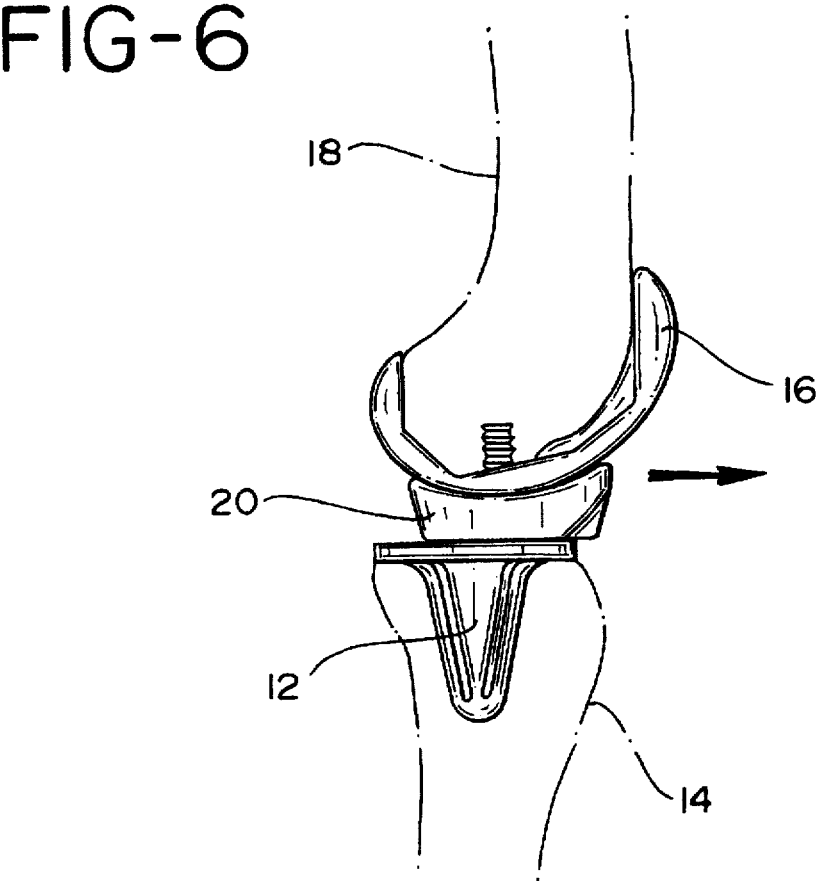
FIG. 6 is a view similar to FIGS. 2 and 4 but showing the femoral component and therewith the bearing element displaced anteriorly.
Figure 7:
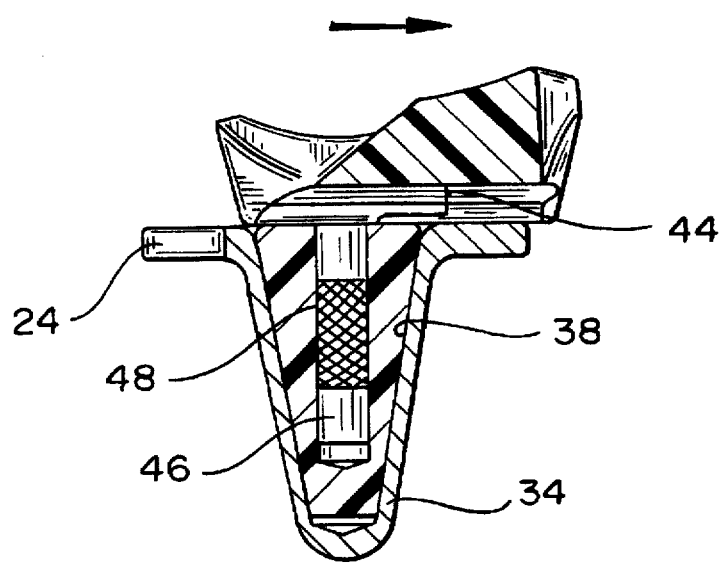
FIG. 7 is a view similar to FIGS. 3 and 5 but showing the joint in the position depicted in FIG. 6.
Figure 8:
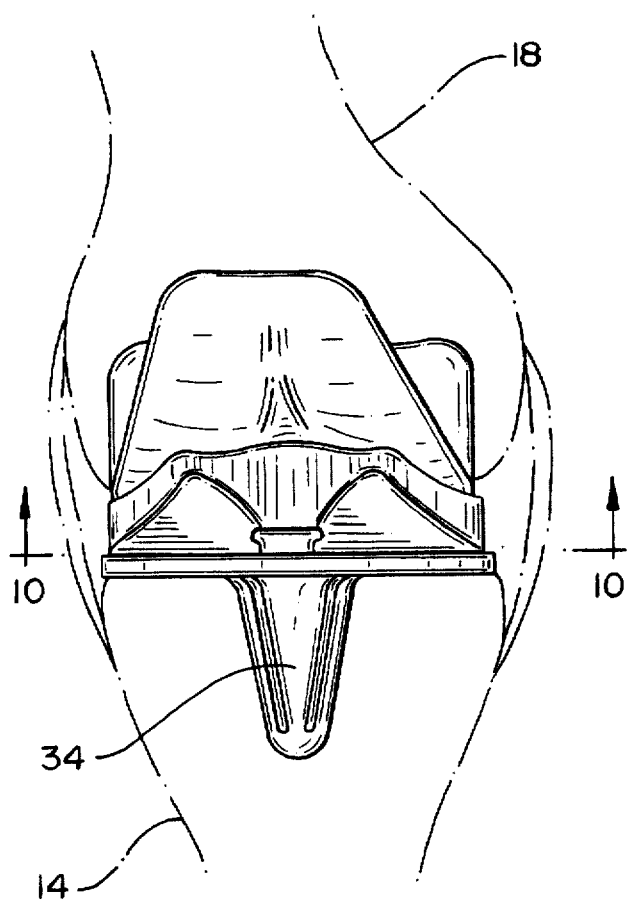
FIG. 8 is an anterior elevational view of the prosthesis of FIG. 1.
Figure 9:
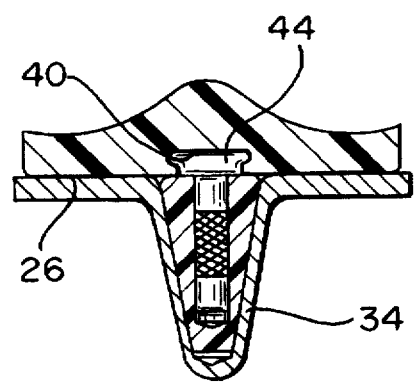
FIG. 9 is a partial cross-sectional view through the plane 9—9 of FIG. 3.
Figure 10:
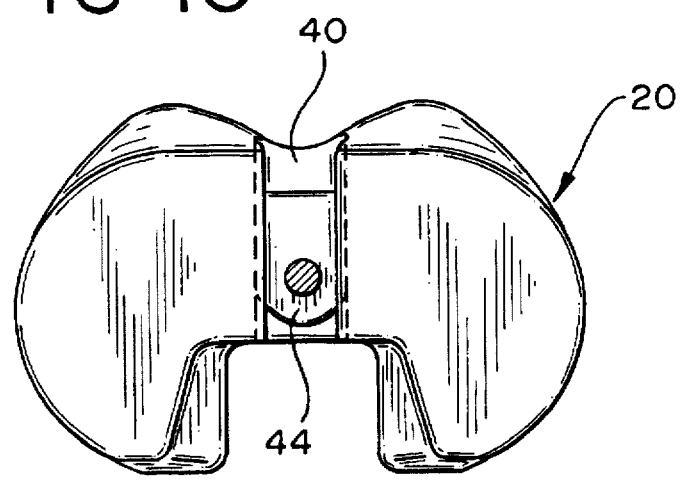
FIG. 10 is a cross-sectional view through the plane 10—10 of FIG. 8.

Referring therefore to FIG. 1, there is shown a total knee prosthesis according to the present invention which is designated generally by the reference numeral 10. Prosthesis 10 includes a tibial element 12 which is rigidly secured to the tibia 14 of a patient, a femoral element 16 which is rigidly secured to the femur 18 of a patient, a bearing element 20 disposed between the tibial element 12 and the femoral element 16, the bearing element 20 being in articulating contact with the tibial element 12 and the femoral element 16; and an intermediate element 22 (FIGS. 3, 11) which is rotatably received within tibial element 12 and slidably received within bearing element 20 to permit selective translation and rotation of bearing element 20 relative to tibial element 12.

Figure 11:
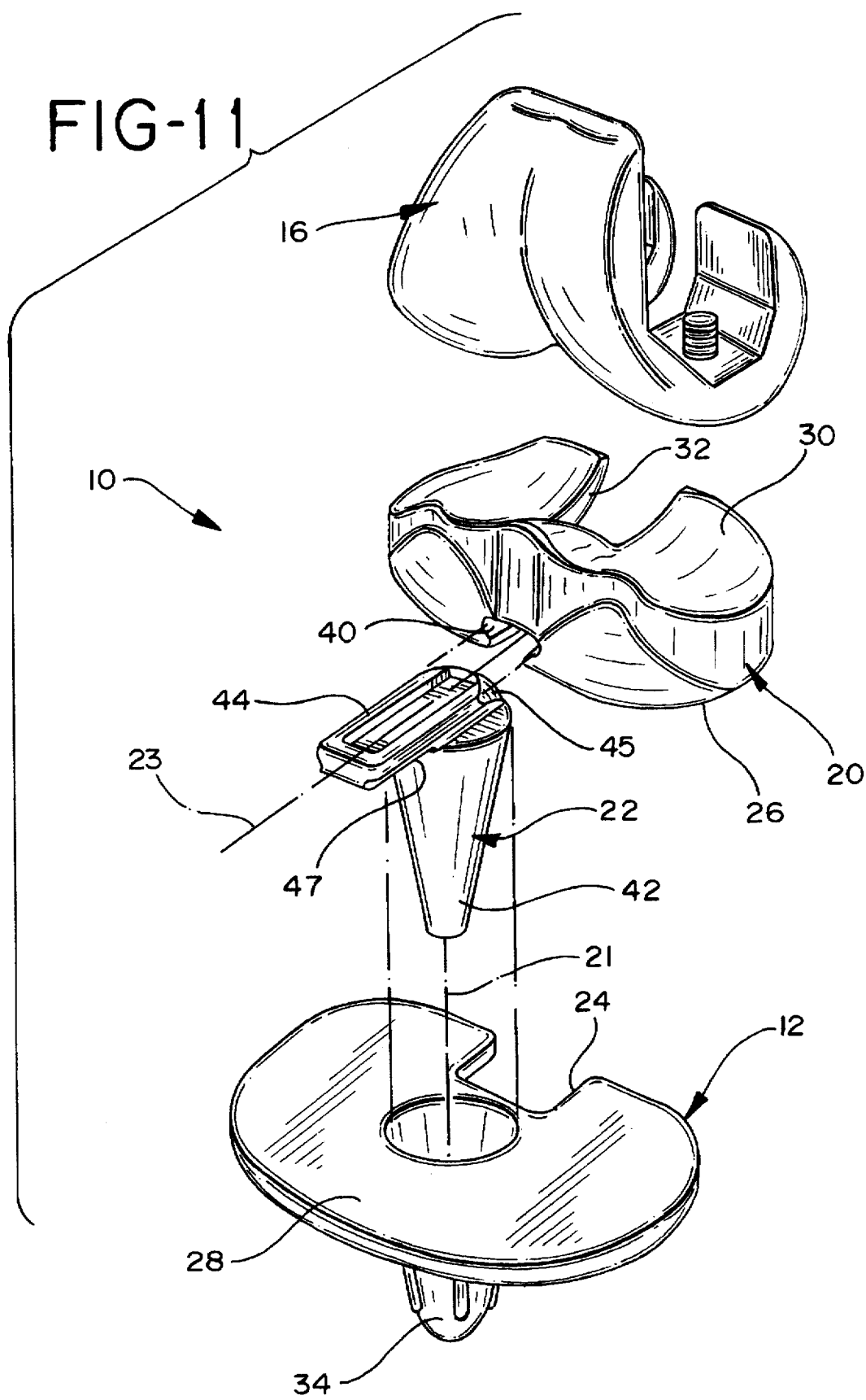
FIG. 11 is an exploded view of a prosthesis according to the present invention.

For purposes of the present disclosure, the term "rotation" as used with respect to movement of bearing element 20 means rotation about the major axis of rotation 21 of tibial element 12 (FIG. 11). The term "translation" as used with respect to the movement of bearing element 20 means displacement of the bearing in a direction parallel to the longitudinal axis 23 (FIG. 11) of the intermediate element 22. Further, the term "lateral displacement" as used with respect to bearing element 20 means a movement which, if permitted, would be perpendicular to the axes 21 and 23 (FIG. 11) of tibial element 12 and intermediate element 22 respectively.

Considering initially femoral element 16, that element is structured and affixed exactly as disclosed in our above-identified prior patents, e.g. femoral component 100 of U.S. Pat. No. 4,470,158. Tibial element 12 is structured substantially identically to tibial component 101 of U.S. Pat. No. 4,470,158 except that tibial element 12 is provided with a recess or notch 24 (FIG. 11) formed in its posterior edge for accommodating the passage therethrough of retained tibial bone and posterior cruciate ligaments, as the case may be.

Referring particularly to FIG. 11, bearing element 20 includes a first bearing surface 26 which is generally planar and adapted to be slidably received on the superior surface 28 of tibial element 12, and a second bearing surface 30 which is structured in accordance with the teaching of the structure of bearing surface 70 of U.S. Pat. No. 4,470,158.

The posterior edge of bearing element 20 is relieved to define a notch 32 which cooperates with notch 24 in tibial element 12 to provide access for the passage of viable posterior cruciate ligaments or tibial bone structure, as the case may be.

As best may be seen in FIGS. 3, 5, 7, 8, 9 and 11, tibial element 12 includes a generally conical projection 34 which is structured to be rigidly received within and secured to tibia 14. Conical projection 34 contains a generally conical recess 38 which is adapted to rotatably receive intermediate element 22 as is discussed below in detail.

The lower surface 26 of bearing element 20 is relieved to define a generally dove-tail-shaped slot 40, the longitudinal axis of which extends through bearing element 20 in the anterior-posterior direction. Slot 40 is adapted to slidably receive therein the guide section 44 of intermediate element 22 as is discussed below in detail.

Referring therefore to FIGS. 3, 5, 7, 9 and 11, intermediate element 22 can be seen to comprise a generally conical section 42 and a guide section 44. Guide section 44 is generally dove-tailed in cross-sectional configuration (FIGS. 9 and 11) so as to be slidably received in substantial surface-to-surface contact within slot 40 of bearing element 20. The posterior edge 45 (FIG. 11) may be curved and tapered so as to reduce the likelihood of ligament damage which might otherwise result from abrasion against the intermediate element 22. Additionally, the taper and curvature of posterior edge 45 facilitates assembly of intermediate element 22 and bearing element 20. It should also be noted that the lower surface of guide section 44 is relieved to define a surface 47 which is spaced from the upper surface of conical section 42. Relief of the lower surface of the guide section in this manner precludes metal-to-metal contact between the lower surface of the guide section and the bearing surface 28 of tibial element 12.

Rigidly secured to the lower surface of guide section 44 is a shaft 46 (FIGS. 3, 5, 7, 9), a portion 48 of the surface of which is knurled. Shaft 46 is rigidly secured, e.g., by press fitting, to conical bearing section 42. The longitudinal axis of shaft 46 is coaxial with the major axis of rotation 21 of intermediate element 22. Conical bearing section 42 may be manufactured from an ultra high molecular weight polyethylene, and is slidably rotatably received within conical recess 38 in conical projection 34 of tibial element 12.

Prosthesis 10 is implanted by first resectioning the femur and tibia as appropriate. With femur 18 and tibia 14 flexed, e.g. to approximately 120° of flexion, tibilar element 12 is then positioned on the head of the tibia 14. Intermediate element 22 is then assembled to bearing element 20 by slidably inserting guide section 44 within bearing slot 40. With the guide section and bearing element so assembled, intermediate element 22 is positioned within tibial element 12 by inserting conical section 42 within conical recess 38 in conical projection 34 of tibial element 12. Femoral element 16 is then implanted on the resectioned distal femur as a result of which the bearing surface of femoral element 16 is in contact with the second bearing surface 30 of bearing element 20.

With the prosthesis so assembled, the bearing surface of femoral element 16 is in contact with bearing surface 30 of bearing element 20, and bearing surface 26 of bearing element 20 is in congruent contact with the bearing surface 28 of tibial element 12. Additionally, bearing element 20 may rotate with intermediate element 22 about axis 21 and may translate in the direction of axis 23 (FIG. 11) of guide section 44. The cooperation of guide section 44 with slot 40 precludes lateral displacement of the bearing element with respect to guide section 44. Thus, the movement of bearing element 20 with respect to tibial element 12 is limited to two degrees of freedom.

Figure 4:
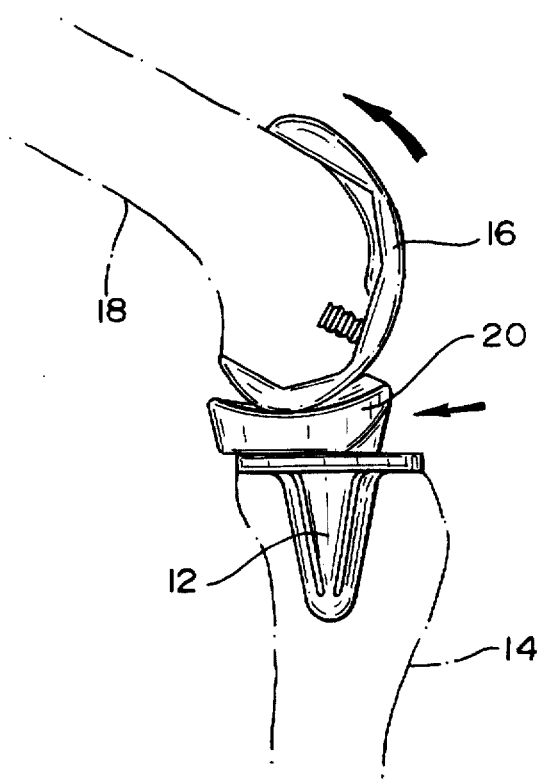
FIG. 4 is a view similar to FIG. 2 but showing the knee in a flexed condition with the bearing translated posteriorly.

Considering now the operation of prosthesis 10, the relative positions of the respective prosthesis elements is shown in FIGS. 1, 2, 3 and 8 for the knee near full extension. As best may be seen in FIGS. 4 and 5, as knee flexion occurs the femoral element 16 slides posteriorly with respect to the tibia 14 causing a posterior displacement of bearing element 20 with respect to tibial element 12. In the course of this flexure movement, any rotation of the femur with respect to the tibia is accommodated by the rotation of bearing element 20 with intermediate element 22, both with respect to tibial element 12. Lateral movement of bearing element 20 with respect to intermediate element 22 is precluded by the cooperation of guide section 44 with slot 40.

As will be recognized by those skilled in these arts, all rubbing contact is between metal and plastic surfaces. Thus, the metal bearing surface of femoral element 16 articulates in contact with the surface 30 of plastic bearing element 20, the metal bearing surface 28 of tibial element 12 articulates in congruent contact with the plastic bearing surface 26 of bearing element 20, the surface of plastic conical bearing section 42 of intermediate element 22 articulates in congruent contact with the metal conical surface 38 of conical projection 34 of tibial element 12, and the metal surface of guide section 44 of intermediate element 22 articulates in congruent contact with the plastic surface of slot 40 in bearing element 20. The articulation of metal with plastic in all modes of operation of the prosthesis 10 is important in avoiding the generation of metallic debris which results from metal-to-metal contact or the occurrence of excessive wear which results from plastic-to-plastic contact.

During normal activity of a patient in whom a prosthesis according to the invention has been provided, motion of the femur relative to the tibia is insufficient to produce dislocation or subluxation of bearing element 20 either from the femoral element 16 or from the tibial element 12. Abnormal posterior motion of bearing element 20 resulting from trauma and/or incomplete ligaments is ordinarily restricted against posterior dislocation by interference from soft tissues, particularly the posterior cruciate, or by bone interference, particularly the cruciate bridge segment retained after resectioning of the proximal tibia. Similarly, abnormal anterior motion and possible dislocation of bearing element 20 is inhibited by the soft tissue structures of the front of the knee, particularly by the patella tendon and retinaculum.

It may be desirable, however, to physically limit the translation of the prosthetic bearing either anteriorly or posteriorly as dictated by particular indications of a patient. The present invention contemplates the provision of means to accomplish such a physical limitation.

Figure 12:
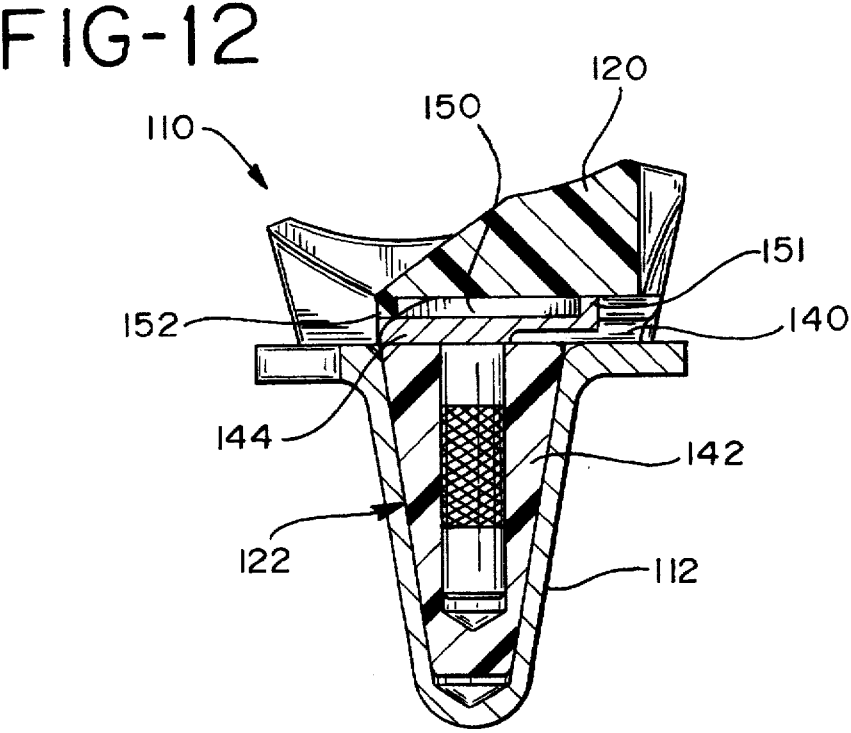
FIG. 12 is a partial cross-sectional view of an alternative bearing structure for use with prostheses according to the present invention.
Figure 13:
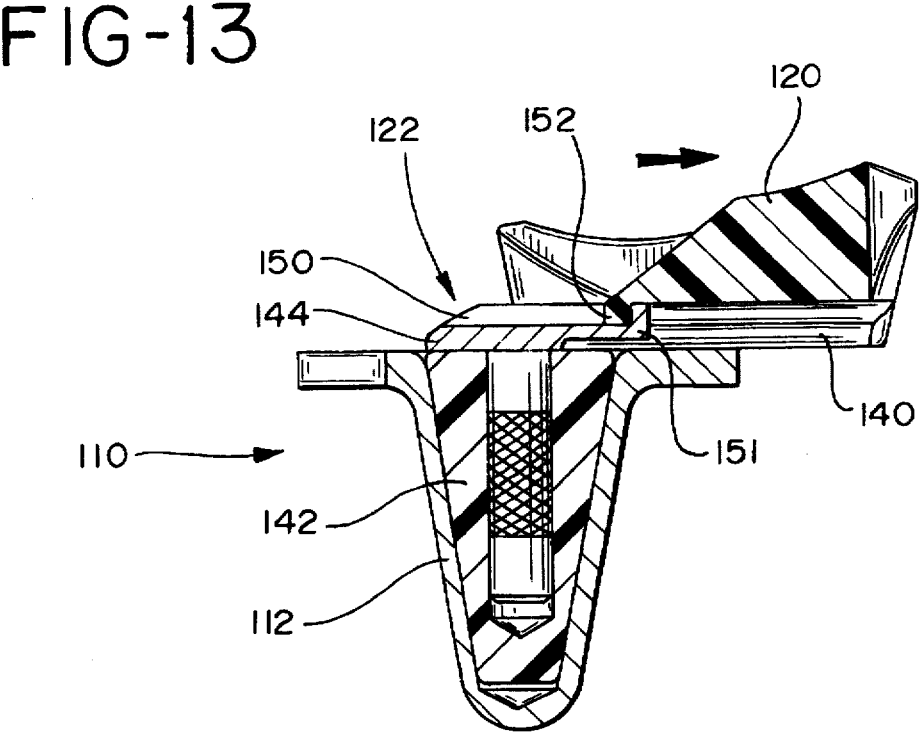
FIG. 13 is a view similar to FIG. 12 showing the bearing element displaced anteriorly; e.g., in response to a traumatic impact to the leg.

Referring therefore to FIGS. 12 and 13, there is shown in cross-sectional views a modified joint prosthesis according to the present invention, which prosthesis is designated generally by reference numeral 110. Prosthesis 110 includes a tibial element 112, a femoral element (not shown), a bearing element 120 disposed between the tibial element 112 and the femoral element in the same manner as discussed with respect to the embodiment of FIGS. 1–11, and an intermediate element 122 which is rotatably received within tibial element 112 and slidably received within dove-tail slot 140 formed in the lower surface of bearing element 120. In this regard, with the exception of the translation limiting means described below in detail, the structures of prostheses 10 and 110 are identical.

Intermediate element 122 comprises a generally conical bearing section 142 and a guide section 144. Guide section 144 is generally dove-tailed in cross-sectional configuration so as to be slidably received in substantial surface-to-surface contact within slot 140 of bearing 120. The upper surface of guide section 144 is relieved throughout a substantial portion of its length (FIG. 11) to define a channel 150 closed at its anterior end by wall 151. It should be noted that channel 150, although depicted in FIG. 11, is not necessary to the structure or operation of prosthesis 10 and may be omitted.

Referring again to FIGS. 12 and 13, it can be seen that the posterior lower edge of bearing element 120 is provided with a downwardly extending shoulder 152. Shoulder 152 is sized to be slidably received within channel 150 of guide section 144.

In normal operation of prosthesis 110, shoulder 152 of bearing 120 and wall 151 of channel 150 are separated, see, e.g., the relative positions of the structures as shown in FIG. 12. In the event of a traumatic impact to the patient's leg which tends to displace the femur anteriorly, bearing element 120 may be moved anteriorly but only to the position where shoulder 152 engages wall 151. Such engagement precludes dislocation of the bearing element 120 from the prosthesis, thus avoiding all the attendant disadvantages.

It should also be recognized that indication for a particular patient may dictate protection against dislocation posteriorly. In such a case, the relieved section in guide element 144 can be reversed so that the channel closure wall is located at the posterior end of the slot rather than as shown in FIGS. 12 and 13. Similarly, in such a situation, the bearing shoulder will be disposed along and dependent from the anterior edge of the bearing. With the shoulder and wall so configured, their engagement will preclude dislocation of the bearing posteriorly.

Thus, there has been described in detail embodiments of joint prosthesis which significantly reduce the likelihood of dislocation of the bearing element, even in response to traumatic stress. It will be recognized by those skilled in these arts that the disclosed embodiments are preferred embodiments and that many modifications and variations to the preferred embodiments may be made without departing from the spirit and scope of the invention.

What is claimed is:

1. An improved prosthetic joint for accommodating articulation between a first bone and a second bone, said joint comprising:

a first element for attachment to a first bone, said first element having a surface facing generally away from said first bone;

a second element for attachment to a second bone, said second element having a surface facing generally away from said second bone;

bearing means disposed between said first and second elements, said bearing means having a first bearing surface in contact with said surface of said first element, and a second bearing surface in contact with said surface of said second element; and intermediate means disposed wholly between said first element and said bearing means for selectively permitting translation of said bearing means, said intermediate means being movable with respect to both said first element and said bearing means, and wherein said bearing means is slidable to permit longitudinal translation with respect to said intermediate means and further including means for preventing transverse translation of said bearing means with respect to said intermediate means.

2. The improved prosthetic joint according to claim 1 wherein said intermediate means is a one-piece integral structure.

3. The improved prosthetic joint according to claim 1 wherein the joint is of the unconstrained type.

4. The joint of claim 1, wherein the intermediate means limits the articulation of the bearing means and the first element to two degrees of freedom.

5. The improved prosthesis according to claim 1 including means for limiting the longitudinal translation between said bearing means and said intermediate means.

6. The improved prosthesis according to claim 5 wherein said means for limiting cooperates with said bearing means and said intermediate means to limit longitudinal translation of said bearing means anteriorly.

7. The improved prosthesis according to claim 5 wherein said means for limiting cooperates with said bearing means and said intermediate means to limit longitudinal translation of said bearing means posteriorly.

8. The improved prosthetic joint according to claim 1 wherein said intermediate means is rotatably mounted on said first element.

9. The improved prosthetic joint according to claim 8 wherein said intermediate means is rotatably mounted on said first element.

10. The improved prosthetic joint according to claim 8 including means for restraining said intermediate means from translation with respect to said first element.

11. The improved prosthetic joint according to claim 10 including means for restraining said intermediate means from rotation with respect to said bearing means.

12. The improved prosthesis according to claim 8 wherein said intermediate means includes a bearing section rotatably received within said first element.

13. The improved prosthesis according to claim 12 wherein said intermediate means includes a head slidably received within said bearing means.

14. The improved prosthesis according to claim 13 wherein said bearing section is rigidly secured to said head.

15. The improved prosthesis according to claim 13 wherein one of said head and said bearing means includes a metal surface and the other of said head and said bearing means includes a plastic surface in sliding contact with said metal surface, and wherein the sliding contact between said head and said bearing means is limited to metal on plastic contact.

16. The improved prosthesis according to claim 13 wherein one of said bearing sections and said first element includes a metal surface and the other of said bearing sections and said first element includes a plastic surface in sliding contact with said metal surface, and wherein the sliding contact of rotation is limited to metal on plastic contact.

17. The improved prosthesis according to claim 13 wherein said head is slidably received in congruent contact with said bearing means.

18. The improved prosthesis according to claim 13 wherein said bearing section is rotatably received in congruent contact within said first element.

19. The improved prosthesis according to claim 13 wherein said head is slidably received within a slot formed in said bearing means.

20. The improved prosthesis according to claim 19 wherein said head and slot cooperate to permit longitudinal translation of said bearing means with respect to said head while precluding transverse translation of said bearing means with respect to said head.

21. The improved prosthesis according to claim 20 and further including means for limiting the longitudinal translation of said bearing means with respect to said head.

22. A prosthetic joint for accommodating articulation between a first bone and a second bone, said joint comprising:

a first metal element for attachment to the first bone, said first metal element having a surface facing generally away from said first bone;

a second element for attachment to the second bone, said second element having a surface facing generally away from said second bone;

plastic bearing means disposed between and in articulating contact with said first and second elements, said plastic bearing means having a first bearing surface in contact with said surface of said first element, and a second bearing surface in contact with said surface of said second element; and intermediate guide means disposed wholly between said first metal element and said plastic bearing means, said intermediate guide means being movably coupled to the first element for permitting the articulation between the first element and the bearing means during normal load bearing operation of the prosthetic joint without metal-to-metal contact between the intermediate guide means and first element, said intermediate guide means selectively permitting translation of said bearing means and being moveable with respect to both said first element and said bearing means, and wherein said bearing means is slidable to permit longitudinal translation with respect to said intermediate guide means and further including means for preventing transverse translation of said bearing means with respect to said intermediate guide means.

23. The joint of claim 22, wherein the guide means is arranged to limit the movement of the bearing means relative to the first element in two degrees of freedom.

24. The joint of claim 22, wherein said guide means comprises a shaft section for rotation with respect to said first element about an axis to provide a rotational degree of freedom of movement between said first element and said bearing means and a first guide section secured to the shaft section, said bearing means including a second guide section mating with the first guide section to provide a second degree of freedom of movement between said first element and said bearing means.

25. The joint of claim 24, wherein the second degree of freedom is translation in a direction transverse said axis.

26. The joint of claim 24, wherein said shaft section includes a metal shaft, said shaft section including a thermoplastic bearing member secured about the shaft and rotatably related to the first element.

27. The joint of claim 26, wherein the bearing means includes guide section receiving means, said first guide section comprises a metal guide member secured to said shaft and slidably received within said guide section receiving means for permitting the bearing means to slide relative to the guide section only in a direction normal to said axis.

28. The joint of claim 27, wherein said metal guide member is spaced from the first element.

* * * * *